(12) United States Patent
Keidar

(10) Patent No.: US 8,066,699 B2
(45) Date of Patent: Nov. 29, 2011

(54) ULTRASOUND ABLATION CATHETER AND METHOD FOR ITS USE

(75) Inventor: Yaron Keidar, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1216 days.

(21) Appl. No.: 11/323,045

(22) Filed: Dec. 30, 2005

(65) Prior Publication Data

US 2006/0122591 A1    Jun. 8, 2006

Related U.S. Application Data

(62) Division of application No. 10/621,988, filed on Jul. 17, 2003, now Pat. No. 7,678,104.

(51) Int. Cl.
    *A61B 18/14* (2006.01)
(52) U.S. Cl. ............... 606/27; 600/439; 606/41
(58) Field of Classification Search ............ 606/27, 606/28, 41, 48–50; 600/439, 466
    See application file for complete search history.

(56) References Cited

U.S. PATENT DOCUMENTS

| | | | |
|---|---|---|---|
| 4,936,281 A * | 6/1990 | Stasz | 600/439 |
| RE34,502 E | 1/1994 | Webster, Jr. | |
| 5,295,484 A * | 3/1994 | Marcus et al. | 600/439 |
| 5,353,798 A | 10/1994 | Sieben | |
| 5,391,199 A | 2/1995 | Ben-Haim | |
| 5,443,489 A | 8/1995 | Ben-Haim | |
| 5,462,521 A | 10/1995 | Brucker et al. | |
| 5,480,422 A | 1/1996 | Ben-Haim | |
| 5,485,845 A | 1/1996 | Verdonk et al. | |
| 5,546,951 A | 8/1996 | Ben-Haim | |
| 5,558,091 A | 9/1996 | Acker et al. | |
| 5,568,809 A | 10/1996 | Ben-Haim | |
| 5,606,974 A * | 3/1997 | Castellano et al. | 600/462 |
| 5,735,280 A | 4/1998 | Sherman et al. | |
| 5,827,278 A | 10/1998 | Webster, Jr. | |
| 5,897,529 A | 4/1999 | Ponzi | |

(Continued)

FOREIGN PATENT DOCUMENTS

WO    WO 95/02995    2/1995

(Continued)

OTHER PUBLICATIONS

European Search Report dated Oct. 5, 2004 for correspondeing European Application No. 04254296.9.

*Primary Examiner* — Michael Peffley
(74) *Attorney, Agent, or Firm* — Christie, Parker & Hale, LLP

(57) ABSTRACT

Catheters and methods for epicardial ablation are provided. A suitable catheter comprises an elongated catheter body and an ultrasound transducer mounted at or near the distal end of the catheter body. The transducer has a front surface and an opposing back surface, wherein the transducer is positioned to transmit ultrasound energy toward tissue facing the front surface but not toward tissue facing the back surface. A sensor is mounted within the catheter near the ultrasound transducer for sensing a location and an orientation of the ultrasound transducer within a patient. A suitable method involves introducing the distal end of the catheter introducing into the pericardium of a patient. The transducer's front surface is positioned so that it generally faces tissue to be ablated, and the tissue is ablated with ultrasound energy generated by the transducer.

17 Claims, 6 Drawing Sheets

U.S. PATENT DOCUMENTS

| | | | |
|---|---|---|---|
| 5,964,757 A | 10/1999 | Ponzi | |
| 6,004,269 A | 12/1999 | Crowley et al. | |
| 6,024,739 A | 2/2000 | Ponzi et al. | |
| 6,120,476 A * | 9/2000 | Fung et al. | 604/95.04 |
| 6,123,699 A | 9/2000 | Webster, Jr. | |
| 6,161,543 A | 12/2000 | Cox et al. | |
| 6,171,275 B1 | 1/2001 | Webster, Jr. | |
| 6,171,277 B1 | 1/2001 | Ponzi | |
| 6,183,435 B1 | 2/2001 | Bumbalough et al. | |
| 6,183,463 B1 | 2/2001 | Webster, Jr. | |
| 6,198,974 B1 | 3/2001 | Webster, Jr. | |
| 6,203,507 B1 | 3/2001 | Wadsworth et al. | |
| 6,210,407 B1 | 4/2001 | Webster | |
| 6,235,024 B1 * | 5/2001 | Tu | 606/41 |
| 6,245,020 B1 | 6/2001 | Moore et al. | |
| 6,248,074 B1 | 6/2001 | Ohno et al. | |
| 6,248,075 B1 | 6/2001 | McGee et al. | |
| 6,267,746 B1 | 7/2001 | Bumbalough | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,394,956 B1 * | 5/2002 | Chandrasekaran et al. | 600/439 |
| 6,514,249 B1 | 2/2003 | Maguire et al. | |
| 6,571,131 B1 | 5/2003 | Nguyen | |
| 6,591,129 B1 | 7/2003 | Ben-Haim et al. | |
| 6,773,402 B2 | 8/2004 | Govari et al. | |
| 6,953,460 B2 | 10/2005 | Maguire et al. | |
| 2002/0042611 A1 | 4/2002 | Sliwa et al. | |
| 2003/0004439 A1 | 1/2003 | Pant et al. | |
| 2003/0078509 A1 * | 4/2003 | Panescu | 600/509 |
| 2004/0002700 A1 | 1/2004 | Ryan et al. | |

FOREIGN PATENT DOCUMENTS

| | | |
|---|---|---|
| WO | WO 96/05758 | 2/1996 |
| WO | WO 97/24983 | 7/1997 |
| WO | WO 98/29033 | 7/1998 |
| WO | WO 00/23125 A3 | 4/2000 |

* cited by examiner

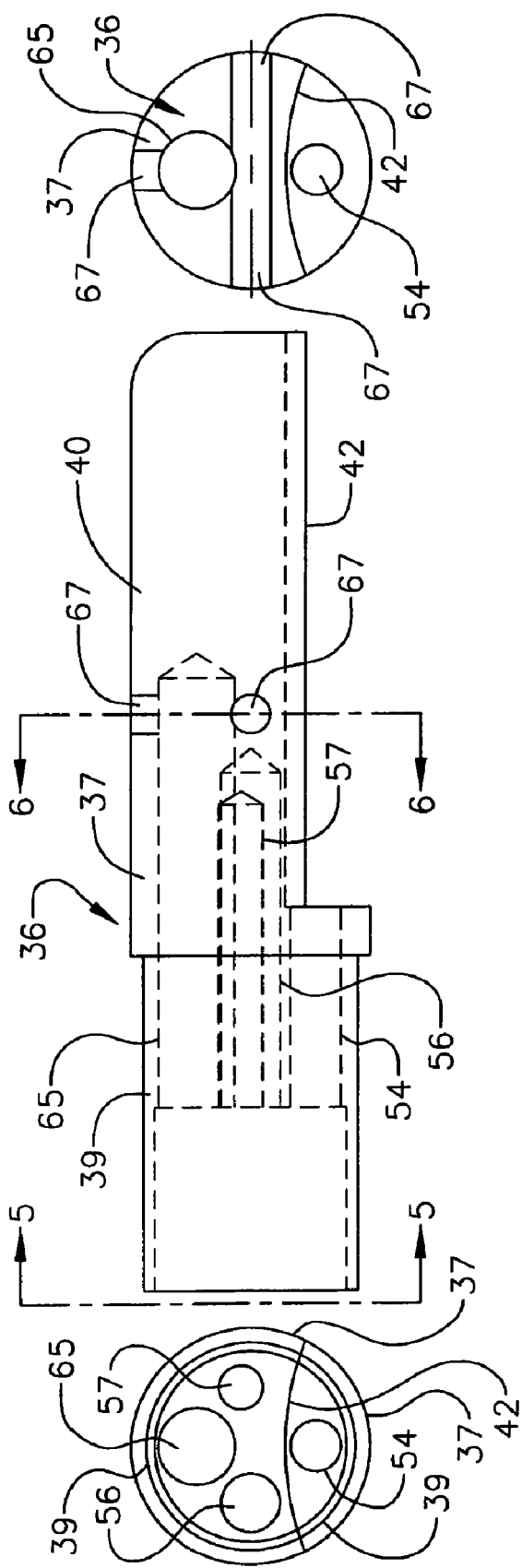

ULTRASOUND ABLATION CATHETER AND METHOD FOR ITS USE

CROSS-REFERENCE TO RELATED APPLICATION(S)

This application is a divisional of U.S. patent application Ser. No. 10/621,988 filed Jul. 17, 2003, now U.S. Pat. No. 7,678,104, the entire contents of which is incorporated herein by reference.

BACKGROUND OF THE INVENTION

Standard radio frequency (RF) ablation, performed using one or more electrode elements, is not very successful for epicardial ablation because it is not directional. RF ablation creates a lesion that burns the tissue in all directions, thereby burning the pericardium. As the burned pericardium heals, it tends to adhere to the epicardial tissue. Further, the lesions created using RF ablation are too shallow to be effective. Thus, a need exists for a catheter that is particularly effective for epicardial ablation.

SUMMARY OF THE INVENTION

The invention is directed to catheters and methods for epicardial ablation using ultrasound energy. In one embodiment, the invention is directed to a catheter that is particularly useful for epicardial ablation. The catheter comprises an elongated catheter body having proximal and distal ends. An ultrasound transducer is mounted at or near the distal end of the catheter body. The transducer has a front surface and an opposing back surface. The transducer is positioned to transmit ultrasound energy toward tissue facing the front surface but not toward tissue facing the back surface. A sensor is mounted within the catheter body near the ultrasound transducer for sensing a location and an orientation of the ultrasound transducer within a patient. With this catheter, the operator can easily determine the precise location and orientation of the ultrasound transducer to assure that the ablation energy is reaching the tissue to be treated.

In another embodiment, the invention is directed to a catheter comprising an elongated catheter body having proximal and distal ends. A tip electrode is mounted at the distal end of the catheter body. The tip electrode has an exposed electrode surface and a transducer mounting surface opposite the exposed electrode surface. An ultrasound transducer is mounted on the transducer mounting surface of the tip electrode.

In yet another embodiment, the invention is directed to a catheter comprising an elongated catheter body having proximal and distal ends. An ultrasound transducer mounted at or near the distal end of the catheter body. The transducer has a front surface and an opposing back surface. The transducer is positioned to transmit ultrasound energy toward tissue facing the front surface but not toward tissue facing the back surface. A control handle is mounted at the proximal end of the catheter body. A deflection wire extends through the catheter body. The deflection wire has a distal end fixedly attached near the catheter body's distal end and a proximal end anchored to a mechanism in the control handle that facilitates longitudinal movement of the deflection wire relative to the catheter body. The deflection wire is anchored at a position that is about 70° to 120° relative to the direction that energy is emitted from the transducer to thereby deflect the distal end of the catheter in a direction generally transverse to the direction that energy is emitted from the transducer.

In still another embodiment, the invention is directed to a method for epicardial ablation in a patient. The method comprises introducing into the pericardium of a patient a distal end of a catheter comprising an elongated tubular body with a transducer mounted at or near the distal end of the tubular body. The transducer has a front surface and an opposing back surface. The transducer is positioned to transmit ultrasound energy toward tissue facing the front surface but not toward tissue facing the back surface. The transducer's front surface is positioned so that it generally faces tissue to be ablated. The tissue to be ablated is then ablated with ultrasound energy generated by the transducer.

BRIEF DESCRIPTION OF THE DRAWINGS

These and other features and advantages of the present invention will be better understood by reference to the following detailed description when considered in conjunction with the accompanying drawings wherein:

FIG. 4 is a side view of a tip electrode according to the invention, with the holes and passages within the tip electrode shown in phantom.

FIG. 5 is an end cross-sectional view of the tip electrode of FIG. 4 along line 5-5.

FIG. 6 is an end cross-sectional view of the tip electrode of FIG. 4 along line 6-6.

DETAILED DESCRIPTION OF THE INVENTION

Figure 1:
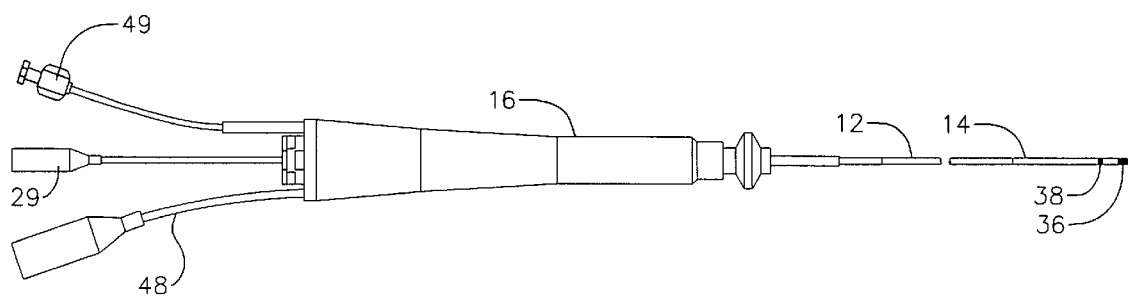
FIG. 1 is a side view of an embodiment of the catheter of the invention.

As shown in FIG. 1, the catheter comprises an elongated catheter body 10 including a proximal shaft 12 and a distal shaft 14 and a control handle 16 at the proximal end of the proximal shaft.

Figure 2:
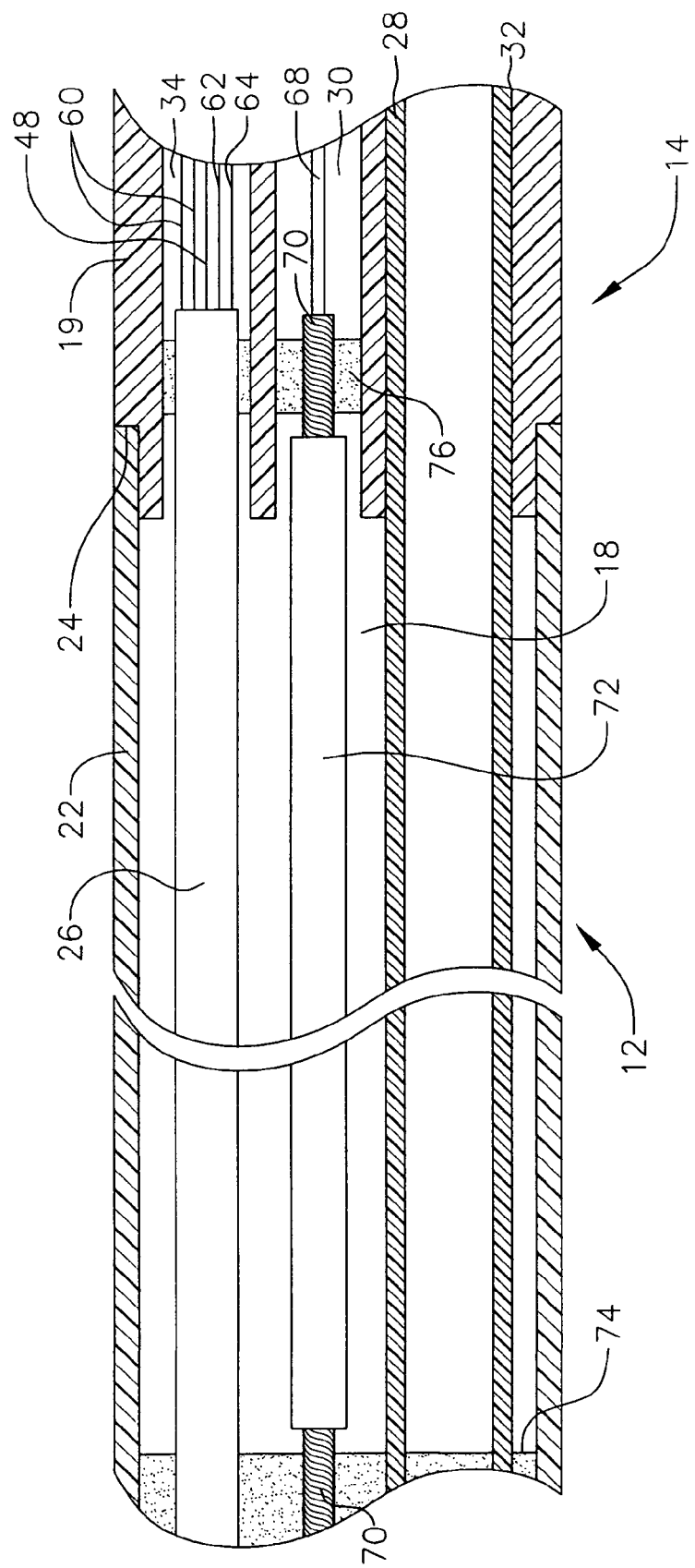
FIG. 2 is a side cross-sectional view of a catheter body according to the invention, including the junction between the proximal shaft and distal shaft.

With reference to FIG. 2, the proximal shaft 12 comprises an elongated tubular construction having a single, axial or central lumen 18. The proximal shaft 12 is flexible, i.e., bendable, but substantially non-compressible along its length. The proximal shaft 12 can be of any suitable construction and made of any suitable material. A presently preferred construction comprises an outer wall 22 made of a polyurethane or nylon. The outer wall 22 comprises an imbedded braided mesh of stainless steel or the like to increase torsional stiffness of the catheter body 10 so that, when the control handle 16 is rotated, the distal shaft 14 will rotate in a corresponding manner.

The outer diameter of the proximal shaft 12 is not critical, but is preferably no more than about 8 french, more preferably no greater than about 7 french. Likewise the thickness of the outer wall 22 is not critical. If desired, the inner surface of the outer wall 22 may be lined with a stiffening tube (not tube), which, along with the braided outer wall 22, can provide improved torsional stability while at the same time minimizing the wall thickness of the catheter, thus maximizing the diameter of the central lumen 18. An catheter including a stiffening tube is described in more detail in U.S. Pat. No. 6,203,507, the disclosure of which is incorporated herein by reference.

In the depicted embodiment, the distal shaft 14 comprises a short section of flexible tubing 19 having three lumens, a puller wire lumen 30, an irrigation lumen 32, and a cable and wire lumen 34. The tubing 19 is made of a suitable non-toxic material that is preferably more flexible than the proximal shaft 12. A presently preferred material for the tubing 19 is braided polyurethane, i.e., polyurethane with an embedded mesh of braided stainless steel or the like, that is more flexible than the catheter body. The number and size of the lumens is not critical and can vary depending on the various wires, tubes and other components carried by the catheter. In a preferred embodiment, the distal shaft 14 has an outer diameter ranging from about 5 french (0.066 inch) to 8 french (0.105 inch).

One means for attaching the proximal shaft 12 to the distal shaft 14 is illustrated in FIG. 2. The proximal end of the distal shaft 14 comprises an outer circumferential notch 24 that receives the inner surface of the outer wall 22 of the proximal shaft 12. The distal shaft 14 and proximal shaft 12 are attached by glue or the like. Other arrangements for joining the proximal and distal shafts are considered within the scope of the invention. For example, the proximal and distal shafts can be made from a single tubing so that the proximal and distal shafts include the same number of lumens. Alternatively, if a stiffening tube is provided, the stiffening tube can extend slightly beyond the distal end of the proximal shaft 12 (e.g., about 3 mm) and be glued to the proximal shaft, with the proximal end of the distal shaft 14 cored out to receive the distal end of the stiffening tube, creating a lap joint. The lap joint and the butt joint formed between the distal end of the proximal shaft 12 and the proximal end of the distal shaft 14 can be secured with polyurethane glue or the like. In another alternative, the proximal shaft 12 can be thermally fused to the distal shaft 14.

If desired, a spacer (not shown) can be located within the proximal shaft 12 at its distal end, adjacent the proximal end of the distal shaft 14. The spacer provides a transition in flexibility at the junction of the proximal shaft and distal shaft, which allows this junction to bend smoothly without folding or kinking. A catheter having such a spacer is described in U.S. Pat. No. 5,964,757, the disclosure of which is incorporated herein by reference.

Figure 3:
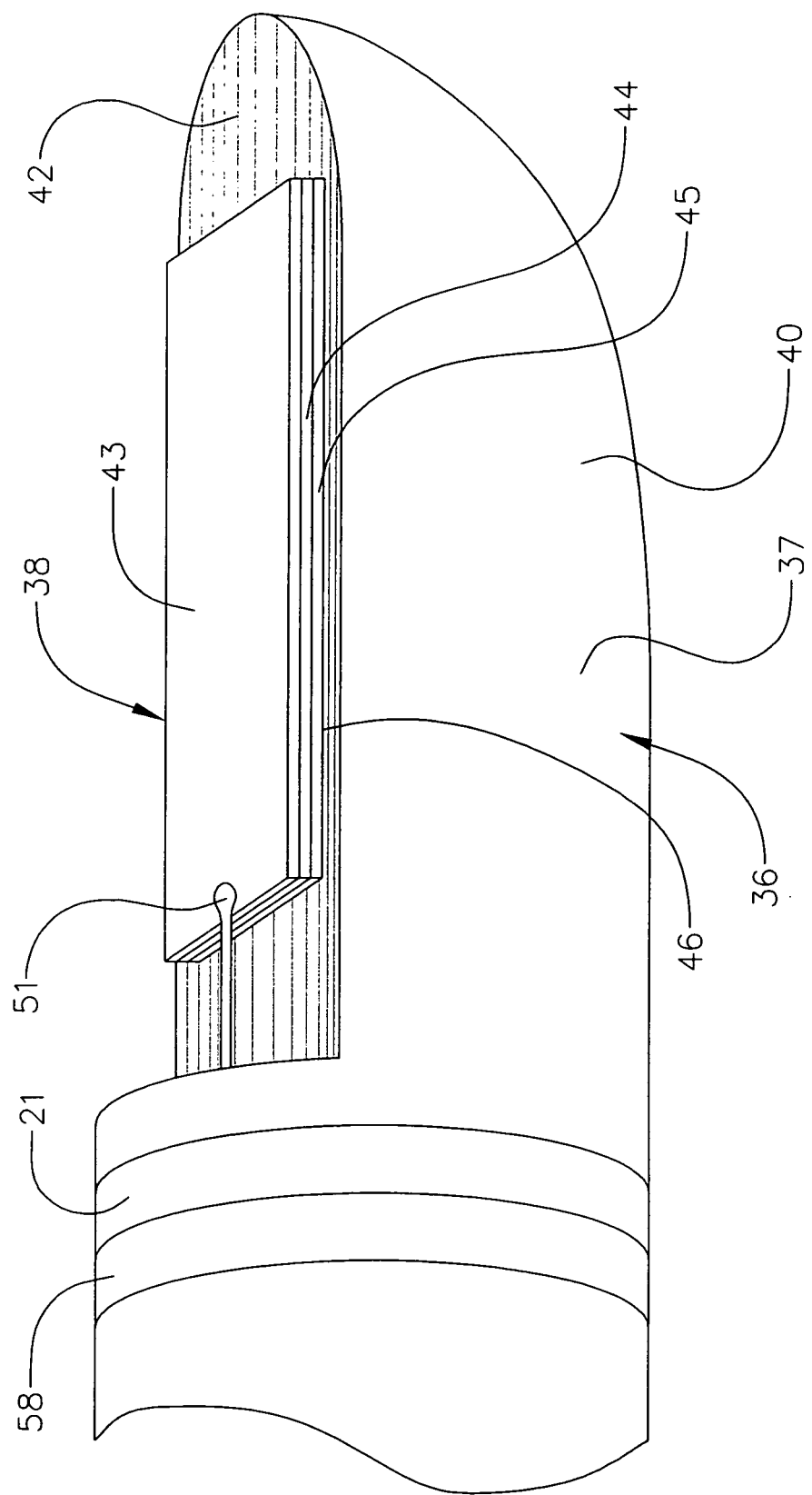
FIG. 3 is a perspective view of a transducer mounted on a tip electrode according to the invention.
Figure 7:
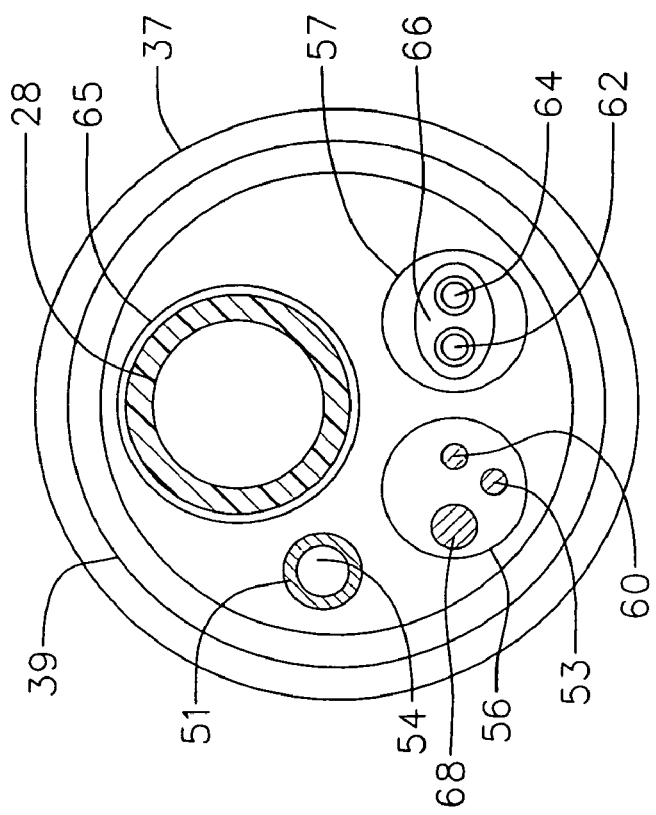
FIG. 7 is an end cross-sectional view of a tip electrode of the invention, including the cable, tube and wires extending into the tip electrode.
Figure 10:
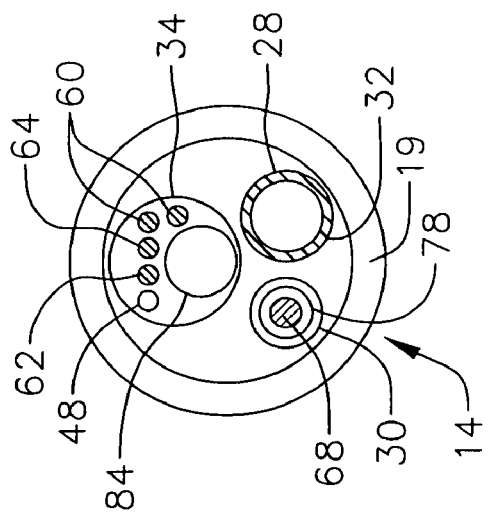
FIG. 10 is an end cross-sectional view of the tubing of the distal shaft shown in FIG. 8 along line 10-10.
Figure 8:
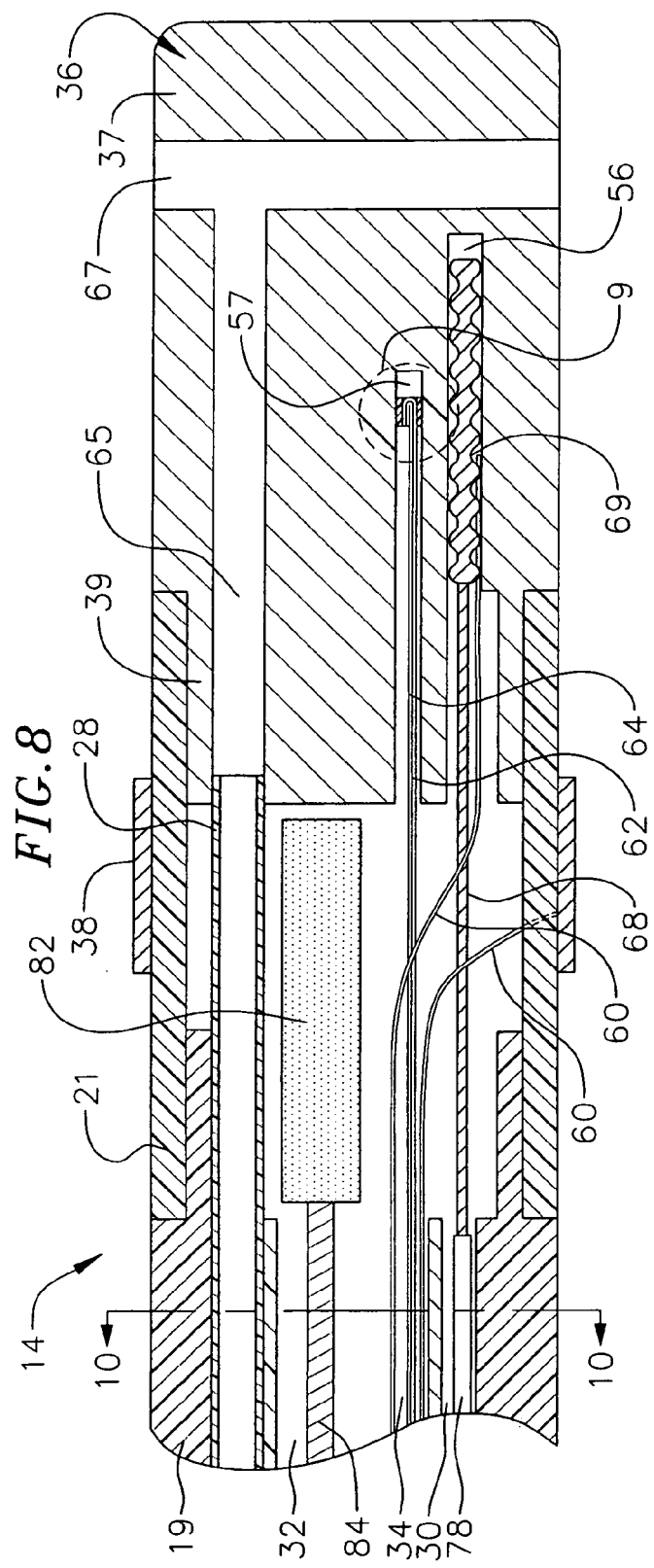
FIG. 8 is a side cross-sectional view of the distal end of a catheter according to the invention showing that extend within the exposed section of the tip electrode.
Figure 9:
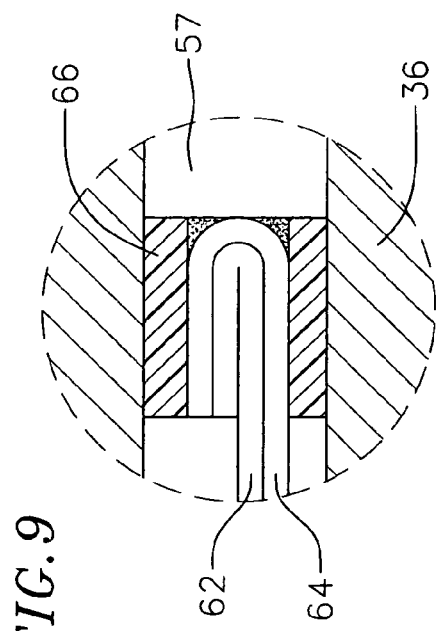
FIG. 9 is an enlarged view of the thermocouple wires mounted in the tip electrode of FIG. 8.

At the distal end of the distal shaft 14 is a tip electrode 36. As shown in FIGS. 3 and 4, the tip electrode 36 has an exposed section 37 having a length ranging preferably from about 2 mm to about 10 mm, more preferably from about 6 mm to about 8 mm, and a stem 39 having a diameter less than the diameter of the exposed section and having a length ranging preferably from about 1 mm to about 6 mm, more preferably from about 2 mm to about 4 mm.

The exposed section 37 of the tip electrode 36 includes an ultrasound transducer 38 mounted thereon. In the depicted embodiment, the exposed section 37 of the tip electrode 36 has an outer ablation surface 40 that is generally co-linear with the outer surface of the tubing 19 and generally rounded like the outer surface of the tubing. The exposed section 37 also includes a cut-out region to provide a transducer surface 42 on which the transducer 38 is mounted. Preferably the cut-out region is sufficiently deep so that, when the transducer 38 is mounted on the transducer surface 42, the transducer does not extend beyond the outer circumference of the tubing 19.

In the depicted embodiment, the transducer 38 comprises three generally-rectangular and generally-flat layers. The central layer 44 is a generally rectangular plate comprising a piezoceramic or piezoelectric crystalline material. The central layer 44 preferably is made of a type PZT-4, PZT-5 or PZT-8, quartz or Lithium-Niobate type piezoceramic material to ensure high power output capabilities. These types of transducer materials are commercially available from Stavely Sensors, Inc. (East Hartford, Conn.) and from Valpey-Fischer Corp. (Hopkinton, Mass.). The outer and inner layers 43 and 45 enclose the central layer 44 and are each constructed of an electrically conductive material, thereby forming transducer electrodes. These outer and inner transducer layers 43 and 45 may each comprise a metallic coating, such as a coating of nickel, copper, silver, gold, platinum, or an alloy thereof. The inner transducer layer 45 can be mounted onto the tip electrode 36 in any suitable manner, for example, by soldering the inner transducer layer to the transducer surface 42 of the tip electrode.

The length of the transducer 38 is selected for a given clinical application and is desirably not longer than the length of the exposed section 37 of the tip electrode 36. The transducer 38 length preferably ranges from about 2 mm to about 10 mm, more preferably from about 5 mm to about 10 mm. The central layer 44 of the transducer 38 has a thickness selected to produce a desired operating frequency. The operating frequency will vary depending upon clinical needs, such as the depth of heating, as well as upon the size of the transducer as limited by the delivery path and the size of the target site. The transducer 38 in the illustrated embodiment preferably operates at a frequency ranging from about 5 MHz to about 20 MHz, and more preferably from about 7 MHz to about 10 MHz. Thus, for example, the transducer can have a thickness of approximately 0.3 mm for an operating frequency of about 7 MHz (i.e., a thickness generally equal to ½ the wavelength associated with the desired operating frequency).

The piezoelectric crystal that forms the central layer 44 of the ultrasound transducer 38 is adapted to contract and expand (or "vibrate") when an alternating current is applied from a current source and across the outer and inner layers 43 and 45. This controlled vibration emits the ultrasonic energy direction away from and generally perpendicular to the generally flat surfaces of the outer and inner layers 43 and 45 to thereby ablate tissue. However, because the inner layer 45 is facing the transducer surface 42 of the tip electrode 36, the energy emitted from the inner layer 45 does not ablate tissue. As a result, ablation can be controlled by directing the ultrasound energy in one direction, i.e., away from the flat surface of the outer layer 43.

The transducer 38 preferably is "air-backed" to produce more energy and to enhance energy distribution uniformity, as is known in the art. In other words, the inner transducer layer 45 does not contact an appreciable amount of the transducer surface 42 of the tip electrode 36. As best shown in FIGS. 5 and 6, the transducer surface 42 of the tip electrode 36 is slightly concave, and the inner transducer layer 45 is generally flat. The bottom edges 46 of the inner transducer layer 45 are soldered to the transducer surface 42, thereby leaving an air-gap between the central region of the inner transducer layer and the transducer surface. The sides and the proximal and distal ends of the transducer 38 are then sealed, for example, with epoxy or a silicone glue (not shown), which is a good sealant and resistant to high temperatures. When the sides and the ends of the transducer 38 are sealed, air is trapped in the air-gap between the transducer and the transducer surface 42 of the tip electrode 36. The air in the air-gap reflects the ultrasound energy directed toward the tip electrode 36 so that the ultrasound energy reverses direction, providing more energy in the desired direction, i.e., toward the tissue to be ablated.

For applying an alternating current from a current source across the outer and inner layers 43 and 45, electrical transducer leads are electrically coupled to outer and inner layers of the transducer 38 by any suitable method. In the depicted embodiment, a coaxial cable 48 is provided, which includes a coaxial center and a coaxial shield. The coaxial center is connected to the outer transducer layer 43 with a coaxial center wire 51 by solder or the like. The coaxial shield 52 is connected to the inner transducer layer 45 by soldering a coaxial shield wire 53 to the coaxial shield and to the tip electrode 36, which, as noted above, is attached to the inner transducer layer. The proximal ends of the coaxial center and coaxial shield of the coaxial cable 48 are adapted to couple to an appropriate ultrasound or radiofrequency generator (not shown).

The coaxial cable 48 extends through the central lumen 18 of the proximal shaft 12 and through the cable and wire lumen 34 of the distal shaft 14. The coaxial center wire 51 extends through a wire passage 54 in the tip electrode 36. As best shown in FIG. 4, the wire passage 54, which extends through the stem 39 and a part of the exposed section 37 of the tip electrode, is on the side of the tip electrode including the cut-out, i.e., the side on which the transducer 38 is mounted. The coaxial shield wire 53 that connects the coaxial shield to the tip electrode 36 extends into a first blind hole 56 in the tip electrode and is soldered within the first blind hole. Other arrangements for the transducer wires are within the scope of the invention.

A radiofrequency (RF) generator (not shown) introduces electrical current to the transducer 36, which converts the electrical current into ultrasonic pressure waves. Alternatively, An ultrasonic generator can be used to generate alternating current to power the transducer 36. The ultrasonic generator drives the transducer at frequencies ranging from about 5 to about 20 MHz, and preferably for the illustrated application ranging from about 7 MHz to about 10 MHz. In addition, the ultrasonic generator can modulate the driving frequencies and/or vary power to smooth or unify the produced collimated ultrasonic beam. For instance, the function generator of the ultrasonic generator can drive the transducer at frequencies ranging from about 6.8 MHz to about 7.2 MHz by continuously or discretely sweeping between these frequencies.

With this design, the transducer 38 has a front surface, i.e., the surface of the outer layer 43 farthest from the transducer surface 42 of the tip electrode 36, and an opposing back surface, i.e., the surface of the inner layer 45 nearest the transducer surface of the tip electrode. The tip electrode 36 prevents the transducer 38 from transmitting ultrasound energy toward tissue facing the back surface, so that the transducer is positioned to transmit ultrasound energy toward only the tissue facing the front surface. The transducer 38 is preferably generally flat, as depicted in FIG. 3, but could be slightly curved if desired. If desired, the transducer 38 can be mounted on the distal shaft 14 instead of on the tip electrode 36.

The tip electrode 36 is connected to the distal shaft tubing 19 by means of a generally rigid tubular plastic housing 21, preferably made of polyether-etherketone (PEEK). The stem 39 of the tip electrode 36 fits inside the distal end of the plastic housing 21 and is bonded to the housing by polyurethane glue or the like. The proximal end of the plastic housing 21 is bonded with polyurethane glue or the like to the distal end of the tubing 19 of the distal shaft 14. It is understood that the tip electrode alternatively may be connected directly to the tubing 19 of the distal shaft 14 as desired as is well known in the art. If desired, the transducer 38 can be mounted on the plastic housing 21 instead of on the tip electrode 36.

In the embodiment shown, a ring electrode 58 is mounted on the distal end of the plastic housing 21. The ring electrode 58 is slid over the plastic housing 21 and fixed in place by glue or the like. If desired, additional ring electrodes may be used and can be positioned over the plastic housing 21 or over the flexible tubing 19 of the distal shaft 14.

The tip electrode 36 and ring electrode 58 are each connected to a separate lead wire 60. The lead wires 60 extend through the plastic housing 21, the cable and wire lumen 34 of the distal shaft 14, the central lumen 18 of the proximal shaft 12, and the control handle 16, and each terminates at its proximal end in an input jack 29 that may be plugged into an appropriate monitor (not shown) and/or source of radio frequency or other ablation energy (not shown). If desired, the portion of the lead wires 60 extending through the proximal shaft 12 and control handle 16 may be enclosed or bundled within a protective tube 26.

The lead wire 60 for the tip electrode 36 is anchored in the first blind hole 56 of the tip electrode by solder or the like. Any other means for electrically-connecting the lead wire 60 to the tip electrode 36 may also be used.

A lead wire 60 is attached to the ring electrode 58 by any conventional technique. Connection of a lead wire 60 to the ring electrode 58 is preferably accomplished by first making a small hole through the plastic housing 21. Such a hole can be created, for example, by inserting a needle through the plastic housing 21 and heating the needle sufficiently to form a permanent hole. A lead wire 60 is then drawn through the hole by using a microhook or the like. The ends of the lead wire 60 are then stripped of any coating and soldered or welded to the underside of the ring electrode 58, which is then slid into position over the hole and fixed in place with polyurethane glue or the like.

A temperature sensor is provided for the tip electrode 36 and, if desired, the ring electrode 58. Any conventional temperature sensor, e.g., a thermocouple or thermistor, may be used. A preferred temperature sensor for the tip electrode 36 comprises a thermocouple formed by an enameled wire pair. One wire of the wire pair is a copper wire 62, e.g., a number 40 copper wire. The other wire of the wire pair is a constantan wire 64. The wires 62 and 64 of the wire pair are electrically isolated from each other except at their distal ends where they are twisted together, covered with a short piece of plastic tubing 66, e.g., polyimide, and covered with epoxy. The plastic tubing 66 is then mounted in a second blind hole 57 in the tip electrode 36, and held in place by polyurethane glue or the like. Alternatively, the wires 62 and 64 can be soldered into the second blind hole 57. In another alternative embodiment, the copper wire 62 of the thermocouple can also be used as a lead wire for the tip electrode 36.

The thermocouple wires 62 and 64 extend through the cable and wire lumen 34 in the distal shaft 14 and through the central lumen 18 of the proximal shaft 12. The wires 62 and 64 then extend out through the control handle 16 and to a connector (not shown) connectable to a temperature monitor (not shown).

An infusion tube 28 is provided for introducing fluid, such as saline, to the tip electrode 36. The infusion tube 28 is preferably made of a biocompatible plastic, such as polyimide. The infusion tube 28 has a distal end anchored in an irrigation passage 65 in the tip electrode 36. In the depicted embodiment, the irrigation passage 65 extends through the stem 39 and into exposed section 37 generally parallel to the axis of the tip electrode 36, but does not extend out the distal end of the tip electrode. Three irrigation branches 67 extend radially from the irrigation passage 65, as best shown in FIG. 6. Irrigation or cooling fluid can be introduced from the infusion tube 28 into the irrigation passage 65 so that the fluid can pass out of the tip electrode 36 through the irrigation branches 67 to thereby cool and/or irrigate the region being ablated.

The infusion tube 28 extends through the irrigation lumen 32 of the distal shaft 14, through the proximal shaft 12, out the proximal end of the control handle 16, and terminates in a luer hub 49 or the like at a location proximal to the control handle. In an alternative arrangement, a single lumen side arm (not shown) is fluidly connected to the central lumen 18 near the proximal end of the catheter body 10, as described in more detail in U.S. Pat. No. 6,120,476, the entire disclosure of which is incorporated herein by reference. Alternatively, the infusion tube 28 can terminate within the distal end of the irrigation lumen 32 of the distal shaft 14, with a second infusion tube (not shown) extending from the proximal end of the infusion lumen, through the proximal shaft 12 and out through the control handle 16. Such a design is also described in more detail in U.S. Pat. No. 6,120,476.

A puller wire 68 (or deflection wire) is provided within the catheter for deflecting the distal shaft 14. The puller wire 68 is anchored at its proximal end to the control handle 16 and anchored at its distal end to the distal shaft 14. The puller wire 68 is made of any suitable metal, such as stainless steel or Nitinol, and is preferably coated with Teflon® or the like. The coating imparts lubricity to the puller wire 68. The puller wire 68 preferably has a diameter ranging from about 0.006 to about 0.010 inches.

A compression coil 70 is situated with the proximal shaft 12 in surrounding relation to the puller wire 68. The compression coil 70 extends from the proximal end of the proximal shaft 12 to the proximal end of the distal shaft 14. The compression coil 70 is made of any suitable metal, preferably stainless steel. The compression coil 70 is tightly wound on itself to provide flexibility, i.e., bending, but to resist compression. The inner diameter of the compression coil 70 is preferably slightly larger than the diameter of the puller wire 68. For example, when the puller wire 68 has a diameter of about 0.007 inches, the compression coil 70 preferably has an inner diameter of about 0.008 inches. The Teflon® coating on the puller wire 68 allows it to slide freely within the compression coil 70. Along its length, the outer surface of the compression coil 70 is covered by a flexible, non-conductive sheath 72 to prevent contact between the compression coil 70 and the lead wires 60 within the proximal shaft 12. A non-conductive sheath 72 made of polyimide tubing is presently preferred.

The compression coil 70 is anchored at its proximal end to the proximal end of the proximal shaft 12 by proximal glue joint 74 and at its distal end to the distal shaft 14 by distal glue joint 76. Both glue joints 74 and 76 preferably comprise polyurethane glue or the like. The puller wire 68 extends into the puller wire lumen 30 of the distal shaft 14. The puller wire 68 is anchored in the first blind hole 56 of the tip electrode 36. In the depicted embodiment, the puller wire lumen 30 and the first blind hole 56 are arranged at an angle of about 70° to about 120°, more preferably about 90°, relative to the direction that energy is emitted from the transducer 38 to thereby deflect the distal end of the catheter in a direction generally transverse to, and preferably generally perpendicular to, the direction that energy is emitted from the transducer.

Preferably, a ferrule 69, made of stainless steel or the like, is crimped onto the distal end of the puller wire 68 to add thickness to the puller wire. The ferrule 69 is then attached to the inside of the first blind hole 56 of the tip electrode 36 with solder or the like. Alternatively, the puller wire 68 can be anchored to the side of the distal shaft 14, as described in U.S. Pat. No. 6,571,131, the disclosure of which is incorporated herein by reference. Within the distal shaft 14, the puller wire 68 extends through into a plastic, preferably Teflon®, sheath 81, which prevents the puller wire 42 from cutting into the wall of the distal shaft 14 when the distal shaft is deflected.

A location sensor 82 is contained within the distal end of the distal shaft 14 for sensing the position and orientation of the transducer 38. In the depicted embodiment, the location sensor 82 is mounted primarily within the plastic housing 21. The distal end of the location sensor 82 extends into a trepanned region 84 in the proximal end of the stem 39 of the tip electrode 36. Depending on the length of the location sensor 82, its proximal end can extend into the tubing 19 of the distal shaft 14. The location sensor 82 is fixed in place by polyurethane glue or the like. Alternatively, the location sensor 82 may be mounted proximal to the tip electrode 36. Other arrangement for mounting the location sensor 82 near the tip electrode 36 (and thus near the transducer 38) are within the scope of the invention. The location sensor 82 is mounted preferably within 10 mm, more preferably within 5 mm, of the transducer 38. In a particularly preferred embodiment, the location sensor 82 is positioned directly under the transducer.

The location sensor 82 is connected to a sensor cable 84, which extends through the cable and wire lumen 34 of the distal shaft 14, through the proximal shaft 12 and into the control handle 16. The sensor cable 84 comprises multiple wires encased within a plastic covered sheath. Within or outside the control handle 16, the sensor cable 84 is connected to a circuit board (not shown). The circuit board amplifies the signal received from the location sensor 82 and transmits it to a computer in a form understandable by the computer. Because the catheter is designed for single use only, the circuit board may contain an EPROM chip that shuts down the circuit board approximately 24 hours after the catheter has been used. This prevents the catheter, or at least the location sensor, from being used twice. A catheter having a control handle in which a circuit board is housed is described in U.S. Pat. No. [insert], the disclosure of which is incorporated herein by reference.

Preferably each location sensor 82 is an electromagnetic location sensor. For example, each location sensor 82 may comprise a magnetic-field-responsive coil, as described in U.S. Pat. No. 5,391,199, or a plurality of such coils, as described in International Publication WO 96/05758. The plurality of coils enables the six-dimensional coordinates (i.e. the three positional and the three orientational coordinates) of the location sensor 80 to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480, 422, 5,546,951, and 5,568,809, and International Publication Nos. WO 95/02995, WO 97/24983, and WO 98/29033, the disclosures of which are incorporated herein by reference.

Longitudinal movement of the puller wire 68 relative to the proximal shaft 12, which results in deflection of the distal shaft 14, is accomplished by manipulation of the control handle 16. Examples of suitable control handles suitable for use in the present invention are disclosed, for example, in U.S.

Pat. Nos. Re 34,502 and 5,897,529, the entire disclosures of which are incorporated herein by reference.

If desired, two or more puller wires can be provided to enhance the ability to manipulate the distal shaft. In such an embodiment, a second puller wire and a surrounding second compression coil extend through the proximal shaft and into an additional off-axis lumen in the distal shaft. If desired, the first puller wire can be anchored proximal to the anchor location of the second puller wire. Suitable designs of catheters having two or more puller wires, including suitable control handles for such embodiments, are described, for example, in U.S. Pat. Nos. 6,123,699, 6,171,277, 6,183,435, 6,183,463, 6,198,974, 6,210,407, and 6,267,746, the disclosures of which are incorporated herein by reference.

In use, the catheter is introduced into a patient so that the distal end of the catheter is positioned in or around a patient's heart. The catheter is particularly suitable for epicardial ablation. With epicardial ablation, the distal end of the catheter is introduced into the pericardium by any suitable technique. Examples of techniques that can be used in connection with the present invention include those disclosed in U.S. Pat. Nos. 6,161,543 and 6,314,963, the disclosures of which are incorporated herein by reference. The distal end is manipulated so that the transducer is generally facing the myocardial tissue. The directional nature of ultrasound energy, discussed above, makes it particularly suitable for ablating the myocardial tissue without also ablating the surrounding pericardial sack. Further, the deep-penetrating nature of the ultrasound energy makes it particularly suitable for burning deep lesions in the myocardial tissue.

Due to the directional nature of the ultrasound energy, it is highly desirable to be able to view the relative positions of the transducer 38 and the myocardial tissue to be ablated. The location sensor 82 permits this information to be easily determined. To use the location sensor 82, the patient is placed in a magnetic field generated, for example, by placing a pad containing coils for generating a magnetic field under the patient. A reference electromagnetic sensor is fixed relative to the patient, e.g., taped to the patient's back, and the catheter containing a second electromagnetic sensor is advanced into the patient's heart. Each sensor comprises three small coils that, in the magnetic field, generate weak electrical signals indicative of their position in the magnetic field. Signals generated by both the fixed reference sensor and the second sensor in the heart are amplified and transmitted to a computer which analyzes the signals and then displays the signals on a monitor. By this method, the precise location of the sensor in the catheter relative to the reference sensor can be ascertained and visually displayed.

Using this technology, the physician can visually map the pericardium or a heart chamber. This mapping is done by advancing the catheter tip into a heart chamber until contact is made with the heart wall. This position and electrograms are recorded and saved. The catheter tip is then moved to another position in contact with the heart wall and again the position is recorded and saved. This procedure is repeated until a three dimensional map of the heart chamber is achieved. The electromagnetic mapping sensor 82 preferably is used in combination with the tip electrode 36 and ring electrode 58. By combining the electromagnetic sensor 82 and electrodes 36 and 58, a physician can simultaneously map the contours or shape of the heart chamber and the electrical activity of the heart.

After such a map is created, the physician can position the catheter with the transducer 38 within the pericardium and use the location sensor 82 to determine and adjust the position and orientation of the transducer relative to the myocardial tissue to be ablated. The transducer 38 is then used to ablate a lesion in the myocardial tissue. The lesion preferably has a depth ranging from about 2 mm to about 5 mm. If desired, both the transducer 38 and tip electrode 36 can be used to ablate tissue. In such an instance, ablation with the tip electrode 36 can be performed before, during or after ablation with the transducer 38.

Saline or other cooling or irrigation fluid can be passed through the irrigation branches 67 in the tip electrode 38 by introducing the fluid into the infusion tube 28 through the luer hub 49. The use of cooling fluid to cool the tissue being ablated reduces or even eliminates burning and charring of the tissue. For example, optimal burns having a depth of 2 to 3 mm were formed at 5 W/15 mL/min. Higher power was found to result in tissue charring and a superficial burn, as the ultrasound energy probably does not penetrate through the char.

As noted above, the puller wire lumen 30 and the first blind hole 56 are arranged at an angle of about 90° relative to the direction that energy is emitted from the transducer 38. With this design, the transducer 38 is mounted parallel to the deflection plane so that, when the catheter is in the pericardium, deflecting it would make the catheter sit flat with the transducer pointing directly into the myocardium.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
    an elongated catheter body having proximal and distal ends, and a longitudinal axis;
    a tip electrode mounted at the distal end of the catheter body, the tip electrode having an exposed electrode surface and a transducer mounting surface, the transducer mounting surface being positioned on an opposite side of the longitudinal axis of the catheter body than the exposed electrode surface, and wherein the tip electrode is fixed and non-rotational relative to the catheter body; and
    an ultrasound transducer mounted on the transducer mounting surface of the tip electrode.

2. The catheter of claim 1, wherein the transducer has a front surface and an opposing back surface that faces the tip electrode, wherein the transducer is positioned to transmit ultrasound energy toward tissue facing the front surface but not toward tissue facing the back surface.

3. The catheter of claim 2, wherein the exposed surface of the tip electrode has a length ranging from about 2 mm to about 10 mm.

4. The catheter of claim 2, wherein the exposed surface of the tip electrode has a length ranging from about 6 mm to about 8 mm.

5. The catheter of claim 1, wherein the tip electrode has an exposed surface and a stem having a diameter less than a diameter of the exposed surface, wherein the transducer is mounted on a surface of the exposed surface.

6. The catheter of claim 1, further comprising a sensor mounted within the catheter body near the ultrasound transducer for sensing a location and an orientation of the ultrasound transducer within a patient.

7. The catheter of claim 6, wherein the sensor is an electromagnetic location sensor.

8. The catheter of claim 1, wherein the transducer is generally flat.

9. The catheter of claim 1, wherein the transducer is generally rectangular.

10. The catheter of claim 1, wherein the transducer has a length ranging from about 2 mm to about 10 mm.

11. The catheter of claim 1, wherein the transducer has a length ranging from about 5 mm to about 10 mm.

12. The catheter of claim 1, further comprising means for deflecting the distal end of the catheter.

13. The catheter of claim 12, wherein the means for deflecting the distal end of the catheter comprises:
   a control handle mounted at the proximal end of the catheter body; and
   a deflection wire extending through the catheter body, the deflection wire having a distal end fixedly attached near the catheter body's distal end and a proximal end anchored to a mechanism in the control handle that facilitates longitudinal movement of the deflection wire relative to the catheter body.

14. The catheter of claim 13, wherein the deflection wire is anchored at a position that is about 70° to 120° relative to the direction that energy is emitted from the transducer to thereby deflect the distal end of the catheter in a direction generally transverse to the direction that energy is emitted from the transducer.

15. The catheter of claim 13, wherein the deflection wire is anchored at a position that is about 90° relative to the direction that energy is emitted from the transducer to thereby deflect the distal end of the catheter in a direction generally perpendicular to the direction that energy is emitted from the transducer.

16. The catheter of claim 1, further comprising an irrigation passage extending through at least a portion of the catheter body and having an open distal end near the transducer to introduce fluid to contact tissue being ablated with the transducer.

17. The catheter of claim 16, wherein the irrigation passage extends through the tip electrode.

* * * * *

UNITED STATES PATENT AND TRADEMARK OFFICE
CERTIFICATE OF CORRECTION

PATENT NO.       : 8,066,699 B2
APPLICATION NO.  : 11/323045
DATED            : November 29, 2011
INVENTOR(S)      : Yaron Keidar It is certified that error appears in the above-identified patent and that said Letters Patent is hereby corrected as shown below:

On the Title Page

(56) References Cited, page 1,     Delete "correspondeing"
Other Publications, line 1.        Insert -- corresponding --

(57) Abstract, line 11.            Delete the second occurrence of "introducing"

Signed and Sealed this
Thirty-first Day of July, 2012

David J. Kappos
*Director of the United States Patent and Trademark Office*